United States Patent [19]

Grummon et al.

[11] Patent Number: 5,314,678
[45] Date of Patent: May 24, 1994

[54] SODIUM IODIDE $^{131}$I CAPSULES

[75] Inventors: Glenn D. Grummon, St. Louis; David E. Helling, St. Charles, both of Mo.

[73] Assignee: Mallinckrodt Medical, Inc., St. Louis, Mo.

[21] Appl. No.: 827,132

[22] Filed: Jan. 28, 1992

[51] Int. Cl.$^5$ ............... A61K 43/00; A61K 49/02
[52] U.S. Cl. ................... 424/1.25; 600/4; 600/7; 424/1.61
[58] Field of Search ............ 424/451, 452, 456, 457, 424/459, 460, 461, 568, 1.1; 428/402.24, 404, 407; 600/3, 4, 7

[56] References Cited

U.S. PATENT DOCUMENTS

| | | | |
|---|---|---|---|
| 2,911,338 | 11/1959 | Tabern et al. | 424/1.1 |
| 3,121,041 | 2/1964 | Stern et al. | 424/1.1 |
| 3,159,545 | 12/1964 | Kidwell et al. | 424/1.1 |
| 3,421,282 | 1/1969 | Hasegawa et al. | 424/1.1 X |
| 4,698,101 | 10/1987 | Koivurinta | 514/23 X |
| 5,049,374 | 9/1991 | Dansereau et al. | 424/1.1 |
| 5,137,723 | 8/1992 | Yamamoto et al. | 424/400 |

FOREIGN PATENT DOCUMENTS

| | | | |
|---|---|---|---|
| 060434 | 9/1982 | European Pat. Off. | |
| 7210728 | 2/1973 | Netherlands | 424/1.1 |
| 2073589 | 10/1981 | United Kingdom | 424/1.1 |

Primary Examiner—Robert L. Stoll
Assistant Examiner—John M. Covert
Attorney, Agent, or Firm—David A. Hey; Brian K. Stierwalt

[57] ABSTRACT

The present invention relates to radiopharmaceutical products used in the treatment of thyroid diseases. In particular, the present invention relates to sodium iodide $^{131}$I capsules which have increased stability and lower volatility.

The objects of the present invention are achieved by providing a $^{131}$I capsule having a matrix material and antioxidant additive combination which provides for increased stability and reduced volatility of the capsule.

5 Claims, No Drawings

SODIUM IODIDE $^{131}$I CAPSULES

BACKGROUND

The present invention relates to radiopharmaceutical products used in the treatment of thyroid diseases. In particular, the present invention relates to sodium iodide $^{131}$I capsules which have increased stability and lower volatility.

The use of $^{131}$I-iodide for the treatment of thyroid disease is known in the prior art. In particular, the administration of millicurie amounts of the $^{131}$I-iodide beta emitting isotope to destroy thyroid tissue is generally accepted as preferable to surgical treatment. This is particularly true when malignant or metastatic processes might be involved. The radioiodide has been effectively supplied in both liquid and capsule form, suitable for oral administration, with the choice between the two apparently based on the preference of the treatment provider.

Because of the highly toxic and volatile nature of iodine, the radioiodide formulations have always presented a relatively high degree of risk to those handling the formulations. To reduce this risk, packages of the $^{131}$I-iodide are generally opened in fume hoods to avoid accidental inhalation of iodine. Further, special storage containers having adsorbent iodine traps are used to ship and store the prepared radioiodide.

The iodide ion itself has no volatility, and therefore, the air-borne spread of radioactivity is believed to be caused by another chemical species. Several species are suspected as the carrier of radioactivity, such a hydriodic acid (HI), hypoiodus acid (HOI), iodine ($I_2$), and organic derivatives such as methyl iodide. The fact that the volatile component reacts with styrofoam, used in the shipping containers, and forms a relatively permanent bond therewith, indicates that the carrier is iodine ($I_2$).

Difficulties in determining the radioactive volatility of iodide solutions, is caused by the presence of a second source of radioactivity within the capsules. Xenon-131m is formed by decay of radioiodide, and may be present in amounts generally of less than 1%. This makes volatility measurements somewhat misleading when the total volatility is, below 0.08%. In particular, at total levels below 0.08%, the amount of radioiodide must be quantified by a detector capable of reading the 364 Kev energy of $^{131}$I. This is because the Xenon-131m has an energy of 164 Kev, which interferes with the standard ion chamber readings. When total volatility is above 0.08%, the volatility may be attributed entirely to iodine.

The volatility of 131I Capsules may be controlled and reduced by including stabilizers within the formulation. In particular, antioxidant materials may be included to reduce the reduction of the non-volatile iodide ion to volatile species as noted above. The addition of antioxidants may be easily included in the known automated capsule formulation process as described below.

Capsules of radioiodide may be prepared in therapeutic doses of up to 100 mCi as calibrated approximately one week after manufacture, by using an automated apparatus. Initially, empty gelatin capsules are separated into a shell and a cap. The shell is then filled with a sieved powder which serves as a matrix material. An aqueous radioiodide solution is then dispensed directly onto the sieved powder. The cap is then placed onto the shell, and the completed capsule is pneumatically transferred to an ion chamber for acceptance assay. The acceptance rate is generally high, as the dispensing apparatus can be made to be very accurate. Those capsules that are accepted, are individually packaged in small containers, along with a adsorbent charcoal packet. The containers are then capped with a screw cap, and then placed within lead shielding. The lead shields are further supported in styrofoam packing in the outer shipping carton.

The small containers may be plastic, however, it has been found that the use of glass vials reduces the amount of escaping radioiodide. Further, design improvements to the screw cap and adsorbent charcoal packet can also help to reduce the amount of escaping radioiodide.

The matrix material used in the formation of capsules, is generally chosen for chemical inertness and physiological compatibility, such as disodium phosphate (heptahydrate). When using disodium phosphate (heptahydrate) as the matrix material, following capsule formation as described above, the aqueous loading solution is gradually transported through the walls of the gelatin capsule. This is caused in part by the inability of the heptahydrate salt to absorb more water after the capping of the capsule. The iodide ion is contained in the aqueous solution and thus is also transported through the gelatin capsule. It is believed that the bioavailability of the transported iodide is different from that of the iodide remaining in the capsule.

The iodide which escapes may undergo oxidation upon contact with surrounding air, to a volatile species such as those described above, and particularly to iodine. The use of antioxidants within the aqueous radioiodide solution acts to reduce the oxidation rate and thus reduce volatility. One known antioxidant is sodium bisulfate which has proven effective in reducing the volatility of $^{131}$I capsules. However, such capsules still exhibit volatility at an undesirably high level, on the order of 700 nCi/mCi/day. Another known capsule formulation uses an antioxidant mixture of disodium phosphate with sodium thiosulfate. Capsules using this formulation and having activity levels up to 50 mCi, exhibit a fairly constant volatility of 17 nCi/mCi/day, or $1.7 \times 10^{-3}$%/day.

However, it is still desirable to reduce volatility of $^{131}$I capsules to lower levels, and to increase stability of the capsules, in order to reduce the radiation risks to those who must handle the capsules and packaging associated therewith.

OBJECTS OF THE INVENTION

It is one object of the present invention to provide a $^{131}$I capsule for use in radiopharmaceutical treatment, having an improved low volatility, and having increased stability.

SUMMARY OF THE INVENTION

The objects of the present invention are achieved by providing a $^{131}$I capsule having a matrix material and antioxidant additive combination which provides for increased stability and reduced volatility of the capsule.

DETAILED DESCRIPTION OF THE INVENTION

It has been discovered that by use of a proper combination of matrix material and antioxidant, that the stability and volatility of $^{131}$I capsules may be optimized. In particular, three different combinations of matrix and antioxidant have been found to maximize stability and minimize volatility.

The first successful combination uses a matrix comprising a blend of fructose with 10% gentisic acid. A radioiodide loading solution which is made 0.25 M in both sodium thiosulfate and sodium ascorbate as antioxidants is deposited on this matrix. Upon deposition, a gum is formed which is believed to prevent the transport of oxygen to the iodide. Capsules formed using this combination have been found to have volatility on the order of $10^{-4}$%/day.

The second successful combination uses a matrix comprising a 10% blend of ascorbic acid in anhydrous sodium pyrophosphate. The radioiodide loading solution is the same as that described above, i.e. made 0.25 M in both sodium thiosulfate and sodium ascorbate as antioxidants. Upon deposition of the loading solution to this matrix, it appears that the water in the loading solution quickly hydrates in the anhydrous sodium pyrophosphate to create a very stable hydrated material. Capsules formed using this combination also exhibit volatility on the order of $10^{-4}$%/day.

The third combination discovered reduces volatility even further. This combination uses the matrix of a 10% blend of ascorbic acid in anhydrous sodium pyrophosphate as described above. The loading solution is treated to be 0.25 M in both sodium thiosulfate and sodium ascorbate, as noted above, and further includes an addition of fructose. The concentration of fructose must be greater than 7.5%. This combination when used in $^{131}$I capsules results in the capsules having volatility on the order of $10^{-5}$%/day.

Therefore, the present invention provides capsules which have greater stability and lower volatility than those known in the prior art. Thus, the capsules according to the present invention are safer to handle and present a lower risk of undesirable radiation exposure.

The following Examples show the improved volatility of $^{131}$I capsules using the combinations of matrix and antioxidants described above, and also describes preferred formulations and methods for making the capsules according to the present invention.

EXAMPLE 1

Preparation Of Capsule Matrix

Sodium pyrophosphate is made anhydrous by drying at 105°–110° C., to a constant weight. To the anhydrous sodium pyrophosphate is added 10% ascorbic acid. The blend is then prepared in a grinder to reduce the particle size. Acceptable mesh size for the grinder is 50–200, which produces particle size of 75–300 μm. The reduced particle size blend is then placed into capsules in amounts of 550–600 mg per capsule.

EXAMPLE 2

Preparation Of Radioiodide Loading Solution

Raw material radioiodide is shipped in 0.1 N sodium hydroxide. To the raw material are added sodium ascorbate and sodium thiosulfate so that the solution is 0.2 M in each antioxidant. Prior to dispensing, fructose is added to give a 10% concentration. The volume dispensed to capsules is generally limited to less than 170 μl. Preferably, the volume dispensed to the capsules in an amount of 50–170 μl. No drying is required.

EXAMPLE 3

Volatility And Stability Determination

Twelve capsules were filled with 550–600 mg of the matrix blend as formed in Example 1. The first six capsules (numbers 1–6) were then loaded with a radioiodide solution made 0.28 M in both sodium ascorbate and sodium thiosulfate. Capsules 1–6 were then capped and placed in test tubes along with a charcoal packet. The loading solution was then diluted with a 40% fructose solution to a level of 10% fructose, which diluted the thiosulfate and ascorbate molarities to 0.21. This diluted solution was used to dispense the second set of six capsules (numbers 7–12), with an equal amount of activity to that of capsules 1–6. Capsules 7–12 were then capped and placed in test tubes along with a charcoal packet. Volatility of all the capsules 1–12 was then determined after three days, and thereafter on a weekly basis. The charcoal packets were replaced on a weekly basis.

Table 1 shows the results of the volatility determinations for capsules 1–12. As is readily apparent, the capsules which included fructose in the loading solution, i.e. capsules 7–12, show much lower volatility than the capsules without added fructose, i.e. capsules 1–6. The lower volatility of capsules 7 remains consistently lower than that of capsules 1–6 even at 24 days from dispensing.

TABLE 1

| CAPSULE NUMBER | % IODINE VOLATILITY | | | |
|---|---|---|---|---|
| | 3 DAYS | 10 DAYS | 17 DAYS | 24 DAYS |
| 1 | $1.5 \times 10^{-4}$ | $4.2 \times 10^{-4}$ | $3.5 \times 10^{-4}$ | $1.8 \times 10^{-4}$ |
| 2 | $1.6 \times 10^{-4}$ | $4.0 \times 10^{-4}$ | $2.4 \times 10^{-4}$ | $1.3 \times 10^{-4}$ |
| 3 | $1.0 \times 10^{-4}$ | $3.7 \times 10^{-4}$ | $3.4 \times 10^{-4}$ | $1.6 \times 10^{-4}$ |
| 4 | $1.3 \times 10^{-4}$ | $4.1 \times 10^{-4}$ | $3.4 \times 10^{-4}$ | $1.9 \times 10^{-4}$ |
| 5 | $1.5 \times 10^{-4}$ | $2.2 \times 10^{-4}$ | $1.7 \times 10^{-4}$ | $1.7 \times 10^{-4}$ |
| 6 | $9.8 \times 10^{-5}$ | $3.3 \times 10^{-4}$ | $1.7 \times 10^{-4}$ | $2.2 \times 10^{-4}$ |
| 7 | $3.1 \times 10^{-5}$ | $5.1 \times 10^{-5}$ | $2.7 \times 10^{-5}$ | $1.2 \times 10^{-5}$ |
| 8 | $3.1 \times 10^{-5}$ | $3.8 \times 10^{-5}$ | — | $2.5 \times 10^{-5}$ |
| 9 | $\sim 5 \times 10^{-6}$ | $2.1 \times 10^{-5}$ | $5.8 \times 10^{-5}$ | $4.4 \times 10^{-5}$ |
| 10 | $2.5 \times 10^{-5}$ | $4.1 \times 10^{-5}$ | $2.7 \times 10^{-5}$ | $3.1 \times 10^{-5}$ |
| 11 | $2.4 \times 10^{-5}$ | $3.2 \times 10^{-5}$ | $9.7 \times 10^{-5}$ | $3.0 \times 10^{-5}$ |
| 12 | $2.2 \times 10^{-5}$ | $6.2 \times 10^{-5}$ | $4.6 \times 10^{-5}$ | $4.4 \times 10^{-5}$ |

EXAMPLE 4

Determination Of Effect Of Pyrophosphate

This experiment was conducted on fourteen capsules (numbers 13–26). Capsules 13 and 14 were filled with a matrix material of powdered disodium phosphate (heptahydrate). Capsules 15 and 16 were filled with a matrix material of a blend of powdered phosphate with 10% ascorbic acid. Capsules 13–16 were then loaded with 50 μl (16 mci) of radioiodide solution made 0.28 M in both sodium thiosulfate and sodium ascorbate. Capsules 13–16 were then capped and placed in test tubes along with a charcoal packet.

Capsules 17 and 18 were filled with powdered phosphate, and capsules 19 and 20 were filled with powdered phosphate with 10% ascorbic acid. The iodide solution above was diluted with 40% fructose to give a 10% solution of fructose and thus diluting the thiosulfate and ascorbate molarities to 0.21. Capsules 17–20 were then each dispensed with 63 μl (16–18 mCi) of the diluted iodide solution. Capsules 17–20 were then capped and placed in test tubes along with a charcoal packet.

Capsules 21–26 were filled with a matrix blend as formed in Example 1, and then loaded with 63 μl (16–18 mCi) of the same diluted iodide solution used in capsules 17-20 above. Capsules 21-26 were then capped and placed in test tubes along with a charcoal packet.

Volatility of capsules 13-26 was then determined after three days and weekly thereafter. In this experiment, the charcoal packets were retained after each assay, and combined with a new charcoal packet, so that the volatility measurements are cumulative. Table 2 shows the results of the volatility determinations for capsules 13-26. In each case where ascorbic acid was added to the matrix material, it was found that volatility was reduced. However, when using the matrix material according to the present invention as formed in Example 1, i.e. sodium pyrophosphate with 10% ascorbic acid, the most drastic reduction in volatility was observed, (capsules 21-26).

TABLE 2

| CAPSULE NUMBER | % IODINE VOLATILITY | | | |
|---|---|---|---|---|
| | 3 DAYS | 10 DAYS | 17 DAYS | 24 DAYS |
| 13 | $1.1 \times 10^{-2}$ | $1.6 \times 10^{-2}$ | $1.7 \times 10^{-2}$ | $1.3 \times 10^{-2}$ |
| 14 | $1.5 \times 10^{-2}$ | $1.8 \times 10^{-2}$ | $2.0 \times 10^{-2}$ | $1.5 \times 10^{-2}$ |
| 15 | $4.7 \times 10^{-3}$ | — | $6.0 \times 10^{-3}$ | $6.5 \times 10^{-3}$ |
| 16 | $1.1 \times 10^{-2}$ | $2.5 \times 10^{-2}$ | $2.8 \times 10^{-2}$ | $2.3 \times 10^{-2}$ |
| 17 | $9.3 \times 10^{-3}$ | $1.9 \times 10^{-2}$ | $2.0 \times 10^{-2}$ | $1.7 \times 10^{-2}$ |
| 18 | $7.6 \times 10^{-3}$ | $2.5 \times 10^{-2}$ | $1.7 \times 10^{-2}$ | $2.3 \times 10^{-2}$ |
| 19 | $2.9 \times 10^{-3}$ | $5.7 \times 10^{-3}$ | $6.3 \times 10^{-3}$ | $5.1 \times 10^{-3}$ |
| 20 | $3.0 \times 10^{-3}$ | $4.2 \times 10^{-3}$ | $5.0 \times 10^{-3}$ | $4.8 \times 10^{-3}$ |
| 21 | $1.4 \times 10^{-5}$ | $2.8 \times 10^{-5}$ | $3.7 \times 10^{-5}$ | $1.1 \times 10^{-4}$ |
| 22 | $3.5 \times 10^{-5}$ | $8.1 \times 10^{-5}$ | $1.0 \times 10^{-4}$ | $1.3 \times 10^{-4}$ |
| 23 | $2.7 \times 10^{-5}$ | $4.4 \times 10^{-5}$ | $7.1 \times 10^{-5}$ | $3.0 \times 10^{-5}$ |
| 24 | $1.9 \times 10^{-5}$ | $5.1 \times 10^{-5}$ | $9.4 \times 10^{-5}$ | $7.4 \times 10^{-5}$ |
| 25 | $3.2 \times 10^{-5}$ | $1.9 \times 10^{-5}$ | $6.8 \times 10^{-5}$ | $7.7 \times 10^{-5}$ |
| 26 | $4.5 \times 10^{-5}$ | $6.5 \times 10^{-5}$ | $9.1 \times 10^{-5}$ | $1.1 \times 10^{-4}$ |

EXAMPLE 5

Loading Capacity Determination

Several capsules filled with the matrix blend as formed in Example 1, were loaded with radioiodide solutions ranging from 50 μl to 170 μl. These capsules were treated for volatility and radiochemical purity. No significant difference was found, thus demonstrating the high liquid loading capacity of the pyrophosphate matrix material.

The Examples above demonstrate the superior stability and volatility of capsules formed using the combinations of matrix material and antioxidants according to the present invention. In particular, the use of pyrophosphate in the matrix blend is shown give greatly improved results over the ordinary phosphate matrix known in the prior art. In addition, the stability of a certain number of capsules prepared according to the present invention, has been demonstrated in excess of 24 days. Radiochemical purity of greater than 95% has been found in such capsules.

In each of the Examples above, the radioiodide solution was received from a supplier in a 0.1 N sodium hydroxide solution, with no antioxidant or inert gas cover. Upon receipt, each radioiodide solution was tested for radiochemical purity using USP paper chromatography. No traces of periodate were observed. Formation of the radioiodide solution according to the preparation process described in Example 2 eliminates the need to rely on the supplier to maintain chemical purity.

The foregoing has been a description of certain preferred embodiments of the present invention, but is not intended to limit the invention in any way. Rather, many modifications, variations and changes in details may be made within the scope of the present invention.

What is claimed is:

1. A $^{131}$I capsule having improved stability and reduced volatility, said capsule having a matrix material and a radioiodide loading solution, wherein said matrix material comprises a 10% blend ascorbic acid in anhydrous sodium pyrophosphate, and said radioiodide loading solution is made 0.25 M in both sodium thiosulfate and sodium ascorbate and further includes fructose.

2. A $^{131}$I capsule according to claim 1, wherein said fructose is added in a concentration of at least 7.5%.

3. A $^{131}$I capsule according to claim 1, wherein said matrix material has a particle size of 75-300 μm, and is included in said capsule in an amount of 550-600 mg.

4. A $^{131}$I capsule according to claim 1, wherein said radioiodide loading solution is included in said capsule in an amount of 50-170 μl.

5. A $^{131}$I capsule having improved stability and reduced volatility, said capsule having a matrix material and a radioiodide loading solution, said matrix material comprising a blend of fructose with 10% gentisic acid, and said radioiodide loading solution is made 0.25 M in both sodium thiosulfate and sodium ascorbate.

* * * * *